(12) United States Patent
Hoefer et al.

(10) Patent No.: US 7,560,590 B2
(45) Date of Patent: Jul. 14, 2009

(54) RECTIFICATIVE SEPARATION OF AN ACRYLIC ACID-CONTAINING LIQUID

(75) Inventors: Frank Hoefer, Ludwigshafen (DE); Volker Schliephake, Schifferstadt (DE); Klaus Joachim Mueller-Engel, Stutensee (DE)

(73) Assignee: BASF Aktiengesellschaft, Ludwigshafen (DE)

(*) Notice: Subject to any disclaimer, the term of this patent is extended or adjusted under 35 U.S.C. 154(b) by 908 days.

(21) Appl. No.: 10/939,498

(22) Filed: Sep. 14, 2004

(65) Prior Publication Data

US 2005/0077240 A1    Apr. 14, 2005

Related U.S. Application Data

(60) Provisional application No. 60/509,540, filed on Oct. 9, 2003.

(30) Foreign Application Priority Data

Oct. 9, 2003    (DE)    ................. 103 47 664

(51) Int. Cl.
*C07C 7/00* (2006.01)
*C07C 51/42* (2006.01)
*B01D 3/10* (2006.01)

(52) U.S. Cl. ............... 562/600; 203/6; 203/9; 203/78

(58) Field of Classification Search ........ 562/600; 203/6, 72, 78, 9
See application file for complete search history.

(56) References Cited

U.S. PATENT DOCUMENTS

| | | | |
|---|---|---|---|
| 5,728,272 A | 3/1998 | Hammon et al. | |
| 5,821,390 A | 10/1998 | Ruppel et al. | |
| 5,831,124 A | 11/1998 | Machhammer et al. | |
| 5,897,749 A * | 4/1999 | Kroker et al. ............ 203/2 |
| 6,063,959 A | 5/2000 | Lehnert et al. | |
| 6,350,352 B2 | 2/2002 | Kroker et al. | |
| 6,413,379 B1 | 7/2002 | Machhammer et al. | |
| 6,455,732 B1 | 9/2002 | Aichinger et al. | |
| 6,498,272 B1 | 12/2002 | Schroeder et al. | |
| 6,679,939 B1 | 1/2004 | Thiel et al. | |
| 2004/0073063 A1 | 4/2004 | Thiel et al. | |
| 2004/0116736 A1 | 6/2004 | Machhammer et al. | |
| 2005/0077240 A1 | 4/2005 | Hofer et al. | |

FOREIGN PATENT DOCUMENTS

| | | |
|---|---|---|
| DE | 195 36 179 | 4/1997 |
| DE | 196 06 877 | 8/1997 |
| DE | 196 27 679 | 1/1998 |
| DE | 197 46 688 | 4/1999 |
| DE | 199 23 389 | 8/2000 |
| DE | 199 24 532 | 11/2000 |
| DE | 199 24 533 | 11/2000 |
| DE | 102 11 273 | 3/2003 |
| DE | 102 13 027 | 3/2003 |
| DE | 102 24 341 | 7/2003 |
| EP | 0 000 110 | 12/1978 |
| EP | 0 700 714 | 3/1996 |
| EP | 0 982 287 | 3/2000 |
| EP | 0 982 289 | 3/2000 |
| EP | 1 033 359 | 9/2000 |
| EP | 1 041 062 | 10/2000 |
| WO | WO 98/08798 | 3/1998 |
| WO | WO 02/076917 A1 | 10/2002 |
| WO | WO 03/051810 | 6/2003 |
| WO | WO 03/064367 | 8/2003 |
| WO | WO 2004/035514 A1 | 4/2004 |

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

A process for rectificatively separating an acrylic acid-containing liquid, by withdrawing an acrylic acid-rich stream from the rectification column above the feed point and polymerization-inhibiting the upper section of the rectification column by means of diacrylic acid.

15 Claims, No Drawings

RECTIFICATIVE SEPARATION OF AN ACRYLIC ACID-CONTAINING LIQUID

The present invention relates to a process for rectificatively separating an acrylic acid-containing liquid F by feeding the acrylic acid-containing liquid F to a rectification column via a feed point Z and withdrawing a stream S at a withdrawal point E above the feed point Z of the rectification column, said stream S having a content of acrylic acid, based on the weight of the stream S, which is $\geq 90\%$ by weight and is greater than the corresponding acrylic acid content of the liquid F in % by weight.

A liquid F at the feed point Z refers to a stream of whose total volume more than 80%, preferably more than 85%, or more than 90%, or more than 95%, or more than 99%, is present as a condensed phase. In other words, the processes of fractional or of total condensation, as described for example, in DE-A 19924532 or in DE-A 19924533, are not encompassed by the present invention.

As a consequence of its very reactive double bond, and also of its acid function, acrylic acid is a viable monomer for preparing polymers which can be used, for example, as water-absorbing resins.

One way of obtaining acrylic acid is by heterogeneously catalyzed partial gas phase oxidation of propene, propane and/or acrolein with oxygen or oxygen-containing gases in the presence of solid catalysts and at elevated temperature (cf., for example, EP-A 700714).

However, this process does not give pure acrylic acid, but rather a product gas mixture which comprises not only acrylic acid but also, as secondary component, unconverted acrolein and/or propene and also constituents such as steam, carbon oxides (CO, $CO_2$), nitrogen, oxygen, propane, methane, lower saturated carboxylic acids such as formic acid, acetic acid and propionic acid, lower aldehydes such as formaldehyde, benzaldehyde, acrolein and furfurals, and also higher carboxylic acids and their anhydrides such as benzoic acid, phthalic anhydride and maleic anhydride.

The acrylic acid is generally basically separated from the gaseous product gas mixture by absorption into a solvent (for example water or organic solvent) or by fractional condensation of the product gas mixture. The resulting condensate or absorbate is subsequently separated rectificatively (generally in a plurality of stages) to obtain more or less pure acrylic acid (cf. WO 03/051810, EP-A 982289, EP-A 982287, DE-A 19606877 and DE-A 10224341). Instead of the fractional condensation, a total condensation may initially be employed and the resulting condensate subsequently worked up rectificatively.

A disadvantage of a rectificative separation of an acrylic acid-containing liquid is that it is a thermal separating process in which the desired separation requires the supply of thermal energy. This is disadvantageous in that acrylic acid in the liquid phase has a tendency to unwanted free-radical polymerization, especially under the action of thermal energy.

Despite the use of free-radical polymerization inhibitors (for example phenothiazine, monomethyl ether of hydroquinone, hydroquinone, N-oxyl radicals, etc), rectificative separations of acrylic acid-containing liquids have to be interrupted from time to time, in order to remove polymer formed in an undesired manner during the rectification from the rectification column (in particular in its upper section) (cf., for example, DE-A 19746688, DE-A 10211273, DE-A 19536179, EP-A 1033359 and DE-A 10213027).

However, such operation shutdowns of rectification columns mean loss of production, which is why enormous efforts are being made worldwide to find improved polymerization inhibitor systems which enable prolonged operation of rectificative separations of acrylic acid-containing liquids.

The latter is especially true of that region of the rectification column which is above the feed point of the acrylic acid-containing liquid to be separated rectificatively into the rectification column. One reason for this is that those secondary components accumulate in this region which are less volatile than acrylic acid. However, various of these comparatively volatile secondary components (for example acrolein) promote the free-radical polymerization tendency of acrylic acid (cf., for example, EP-A 1041062), which is why its inhibition in this region is of particular significance.

However, a disadvantage of the existing processes for rectificatively separating an acrylic acid-containing liquid by feeding the acrylic acid-containing liquid to a rectification column and withdrawing a stream above the feed point of the rectification column, said stream having an acrylic acid content which is $\geq 90\%$ by weight and is greater than the corresponding acrylic acid content of the liquid, is that the polymerization inhibition in the upper section of the rectification column is not fully satisfactory.

It is an object of the present invention to improve this polymerization inhibition.

A further, normally undesired accompanying phenomenon of acrylic acid in condensed phase is the formation of oligomers having $\geq 2$ monomer units by Michael addition of acrylic acid to itself and also to acrylic acid dimers (oligomers) forming as a result. For statistical reasons, it is in particular the formation of diacrylic acid

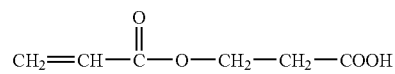

which is significant, whereas the formation of higher acrylic oligomers (trimers, tetramers, etc.) is generally negligible.

Since diacrylic acid has a less marked tendency to free-radical polymerization than acrylic acid, acrylic acid is typically subject to the requirement to contain very little diacrylic acid (cf. DE-A 19923389, DE-A 19627679 and WO-03/064367). This is in particular because diacrylic acid formation is reversible and, in the case of free-radically copolymerized diacrylic acid, the subsequent thermal treatment of the polymer (for example when a water-absorbent resin is dried) may result in monomeric acrylic acid being eliminated, which is generally undesired.

As a consequence of the significantly different boiling points, it is possible to remove diacrylic acid from acrylic acid in a simple manner by rectification. Diacrylic acid accumulates in the lower section of the rectification column and acrylic acid in the upper section of the rectification column which is normally substantially predominantly free of diacrylic acid. This is in particular because the formation of new diacrylic acid is a slow process.

When acrylic acid is left to stand under standard conditions, it takes about 24 h for 150 ppm of diacrylic acid based on the weight of the acrylic acid to be newly formed. The presence of diacrylic acid in the upper section of the rectification column has hitherto been undesired in view of the aforementioned.

However, the basis of the present invention is the surprising finding that the presence of diacrylic acid has a polymerization-inhibiting effect with respect to free-radical polymerization of acrylic acid. This is attributed to diacrylic acid having a distinctly less marked tendency to free-radical polymerization than acrylic acid itself. As a consequence of this reduced polymerization tendency, it is assumed that diacrylic acid distributed in acrylic acid acts like a chain growth terminator on free-radically growing acrylic acid polymer chains.

We have found that this object is achieved by a process for rectificatively separating an acrylic acid-containing liquid F by feeding the acrylic acid-containing liquid F to a rectification column via a feed point Z and withdrawing a stream S at a withdrawal point E above the feed point Z of the rectification column, said stream S having a content of acrylic acid, based on the weight of the stream S, which is ≧90% by weight and is greater than the corresponding acrylic acid content of the liquid F in % by weight, wherein the diacrylic acid content G of the reflux liquid within the region of the rectification column at least two theoretical plates above the feed point Z is at least in places ≧550 ppm by weight based on the weight of the reflux liquid.

Within a rectification column, descending liquid phase (reflux liquid) and ascending vapor phase are conducted in countercurrent to each other. As a consequence of the inequilibrium existing between the streams, there is heat and mass transfer which brings about the desired separation. In general, there are separating internals in a rectification column to increase the mass transfer surface area. Useful such internals, also in the present process, are, for example, structured packings, random packings and/or mass transfer trays of any type.

Mass transfer trays on which there is equilibrium between descending liquid and ascending vapor are referred to as theoretical plates. This term can also be applied to all other separating internals which are suitable for countercurrent rectifications (for example structured packings and random packings).

This document therefore appropriately refers quite generally to theoretical plates. Theoretical plate is defined as that spatial unit which brings about enrichment in accordance with the thermodynamic equilibrium.

The process according to the invention is found to be advantageous especially when the acrylic acid content of the stream S is ≧93% by weight or ≧95% by weight. However, it can also be advantageously employed when the acrylic acid content of the stream S is ≧97% by weight, or ≧98% by weight, or ≧99% by weight, or 99.5% by weight or ≧99.8% by weight.

In the process according to the invention, the diacrylic acid content of the reflux liquid, based on the weight of the reflux liquid, within the region of the rectification column which is at least two (or three, or four, or five) theoretical plates above the feed point Z is preferably, at least in some regions, not only at values of ≧550 ppm by weight, but rather at values of ≧600 ppm by weight, or at values of ≧650 ppm by weight, or at values of ≧700 ppm by weight, or at values of ≧750 ppm by weight, or at values of ≧800 ppm by weight.

Very particular preference is given to this diacrylic acid content G in the process according to the invention being ≧850 ppm by weight, or ≧900 ppm by weight, or ≧950 ppm by weight, or ≧1000 ppm by weight.

Even more advantageously, the aforementioned diacrylic acid content G in the process according to the invention is at values of ≧1250 ppm by weight, or ≧1500 ppm by weight, or ≧1750 ppm by weight, or ≧2000 ppm by weight, or ≧2500 ppm by weight, or ≧3000 ppm by weight.

However, the aforementioned diacrylic acid content will generally not be more than 10 or 5% by weight and normally be at values of ≦3% by weight or ≦2% by weight.

According to the invention, the aforementioned diacrylic acid contents G of the reflux liquid which are favorable in accordance with the invention are appropriately satisfied in that region of the rectification column which is at least two theoretical plates above the feed point Z and which, starting from the withdrawal point E of the stream S, is within the interval from E+0.5 theoretical plate to E+5 theoretical plates.

The process according to the invention is particularly favorable when the aforementioned diacrylic acid contents G of the reflux liquid which are favorable in accordance with the invention are satisfied within the entire region of the rectification column which is at least two, or at least four, or at least six, or at least eight or more, theoretical plates above the feed point Z.

However, the process according to the invention is advantageous even when the withdrawal point E is at least two, or at least four, or at least six, or at least eight or more theoretical plates above the feed point Z and the aforementioned diacrylic acid contents G of the reflux liquid are satisfied within the entire region of the rectification column which is above the withdrawal point E.

According to the invention, the withdrawal point E in the process according to the invention is appropriately at least 2 theoretical plates, or at least 5 theoretical plates, or at least 8 theoretical plates, or at least 10 theoretical plates, or at least 12 theoretical plates, above the feed point Z of the rectification column.

In addition, favorable processes according to the invention for rectificative separation have at least 0.5 theoretical plate, or at least 1 theoretical plate, or at least 1.5 theoretical plates, above the withdrawal point E.

Any diacrylic acid present in the stream withdrawn from the process according to the invention may if required be removed in downstream separating stages. These separating stages may be, for example, of crystallizative or else rectificative nature. One case in which the latter is appropriate is where the rectification is carried out under such conditions that the polymerization tendency of acrylic acid is minimized and no additional inhibition is required by means of the diacrylic acid present in the reflux liquid. The diacrylic acid removed may be dissociated to acrylic acid in a manner known per se (cf., for example, WO 03/048100).

The adjustment of the diacrylic acid content of the reflux liquid which is necessary in accordance with the invention may be realized in various ways. One way is to add a Brønsted acid which is different to acrylic acid and catalyzes the Michael addition of acrylic acid to the reflux liquid (for example at the top of the column). According to the invention, the acid strength of such Brønsted acids, quoted in the form of their $pK_a$ values (at 25° C., 1 atm, water as a solvent; cf. Grundlagen der aligemeinen und anorganischen Chemie [Basics of General and Inorganic Chemistry], H. R. Christen, Verlag Sauerländer, Aarau, 1973, p. 354), is appropriately ≦16, preferably ≦7, more preferably ≦5.

Particularly suitable in accordance with the invention are, for example, $H_2O$ and strong protic mineral acids such as $H_2SO_4$, HCl or $H_3PO_4$. Among these, particular preference is given to volatile mineral acids (i.e. in particular more volatile than acrylic acid, i.e. Brønsted acids having a lower boiling point than acrylic acid and $pK_a \leq 16$). In the lower portion of the rectification column, the catalytic action of the mineral acid may be eliminated again by addition of a neutralizing Brønsted base.

However, instead of a Brønsted acid, a Brønsted base which catalyzes diacrylic acid formation may also be added. According to the invention, the base strength of such Brønsted bases, quoted in the form of their $pK_b$ value (at 25° C., 1 atm, water as a solvent; cf. Grundlagen der organischen Chemie, H. R. Christen, Verlag Sauerländer, Aarau, 1975, p. 392), is appropriately ≦10, preferably ≦8 and more preferably ≦5.

According to the invention, examples of particularly suitable Brønsted bases are aminic Brønsted bases such as methylamine, dimethylamine, trimethylamine, ethylamine, diethylamine, triethylamine, tetramethylethylenediamine, n-propylamine, n-butylamine, benzylamine, pyridine, aniline, urea or ammonia. Among these, particular preference is given to volatile aminic Brønsted bases. It will be appreciated that corresponding aqueous solutions may also be added at the top of the column. In the lower section of the rectification column, the catalytic action of the Brønsted base may be eliminated again by adding a neutralizing Brønsted acid. However, there is in some cases automatic self-elimination of the catalytic action of the Brønsted base toward the lower section of the rectification column by its reaction with acrylic acid at the increasing temperatures toward the bottom of the rectification column to give the corresponding amides which accumulate in the column bottom.

Additionally or alternatively, the addition, for example the aqueous addition, may even be directly into the liquid F to be separated. This is especially true in the case of Brønsted acids or bases which are more volatile than acrylic acid. When the liquid F is obtained by absorbing acrylic acid from reaction gas mixtures from partial oxidations, the addition may be as early as in the course of the absorption.

However, it will be appreciated that the diacrylic acid required may also be added as such to the reflux liquid in the process according to the invention. Diacrylic acid is obtainable, for example, by initially enriching it in acrylic acid and subsequently removing it in a distillative or crystallizative manner. Instead of adding removed diacrylic acid, the high-grade diacrylic acid-containing acrylic acid itself may also be added to the reflux liquid in the upper rectification column section. In a manner which is appropriate from an application point of view, other polymerization inhibitors required in the rectification column will advantageously also be added to this acrylic acid. It will be appreciated that the diacrylic acid in this case will be enriched in acrylic acid whose degree of purity, disregarding any inhibitor present therein, at least corresponds to that of the stream S to be removed in the process according to the invention.

The process according to the invention will of course be carried out with the addition of the other polymerization inhibitors to be added in a manner known per se, for example phenothiazine, monomethyl ether of hydroquinone, N-oxyl radicals, etc. Preference is given to adding these at the top of the column in dissolved (for example in diacrylic acid-containing acrylic acid) or in molten form. However, their consumption rate may be reduced in the process according to the invention.

The process according to the invention is especially suitable when the rectification column is a tray column. This is a rectification column whose separating internals are substantially exclusively mass transfer trays. According to the invention, appropriate rectification columns are those tray columns of whose number of mass transfer trays at least 80% are sieve trays. Advantageously, the tray rectification column to be used in accordance with the invention contains exclusively sieve trays as mass transfer trays. This refers in this document to plates whose passages for the ascending gas or vapor phase (the terms "gaseous" and "vaporous" are used synonymously in this document) are simple holes and/or slots.

The sieve trays to be used are typically differentiated into two groups, i.e. into those having forced liquid flow and those without forced liquid flow.

Quite generally, forced liquid flow is achieved on mass transfer trays by the mass transfer trays having at least one downcomer (drain), through which the reflux liquid flows, irrespective of the flow path of the ascending vapor stream, from the higher tray to the next lowest tray (feed). The horizontal liquid flow over the mass transfer tray from feed to drain is selected in accordance with the task in process technology terms. The gas or the vapor passes through the open cross sections of the mass transfer tray.

When the reflux liquid is conducted in reverse flow over the tray (feed and drain of the mass transfer tray are disposed on the same side of the tray), these are referred to as reverse flow trays. In radial flow trays, the liquid flows radially on the tray from the middle (feed) to the drain at the edge of the tray.

In the crossflow trays, viewed over the entire flow area, the liquid is conducted transversely over the tray from feed to drain. In general, crossflow trays have a single-flow configuration. In other words, feed and drain are disposed on opposite sides of the tray. However, they may also have a double-flow (or more than double-flow) configuration. In this case, the feed may be disposed, for example, in the middle and a drain on each of the opposite sides of the mass transfer tray.

In other words, the forced flow of the reflux liquid is achieved in sieve trays by the sieve trays having, in addition to the passages for the ascending gas or vapor phase, at least one downcomer (drain), through which the reflux liquid, irrespective of the flow path of the vapor, flows from the upper tray to the next lowest tray (feed). The liquid flows, for example, in crossflow over the tray from the at least one feed to the at least one drain, and the feed pipe and drainpipe guarantee the liquid seal and the desired liquid height on the tray. Frequently (especially in the case of low column diameters), the sieve trays with forced liquid flow have a single-flow configuration. In other words, feed and drain are disposed on opposite sides of the mass transfer tray. However, they may also have a double-flow (or more than double-flow) configuration. In this case, the feed may be disposed, for example, in the middle and a drain on each of the opposite sides of the mass transfer tray. Such sieve trays are to be referred to hereinbelow as forced sieve trays. In these trays, trickle-through of the reflux liquid which reduces the separating action is not, as in the case of hydraulically sealed crossflow trays, prevented by chimneys, into which the passages continue, but rather a minimum vapor loading is required for this purpose. The vapor ascends through the passages and bubbles through the liquid layer maintained by the drainpipe.

The dual-flow or else trickle sieve trays differ from the forced sieve trays in that they contain no drain segment. The absence of drain segments (downcomers) in the dual-flow trays results in the ascending gas and the liquid descending in the separating column passing through the same passages of the tray. As in the case of forced sieve trays, a minimum vapor loading is also required in the case of dual-flow trays, in order to achieve appropriate separating action. When the vapor loading is significantly lower, ascending gas and descending reflux move past each other substantially without exchange and the mass transfer tray is at risk of running dry.

In other words, in the case of dual-flow trays too, a lower limiting rate has to be present so that a certain liquid layer is maintained on the tray, in order to allow the tray to work. Within the normal working range, the liquid in dual-flow trays trickles through the passages from tray to tray and the continuous gas phase is interspersed by a divided liquid phase between the trays. According to the invention, preference is given to the aforementioned sieve trays of the rectification column to be used being dual-flow trays.

Preferred sieve tray rectification columns for the process according to the invention are those described in DE-A 10230219. However, equally useful for the process according to the invention are also those sieve tray rectification columns which are described in DE-A 10156988 and in EP-A 1029573.

Compared to sieve trays, hydraulically sealed crossflow trays are characterized in that, when the separating column is shut down, they cannot run dry, disregarding the tiny emptying drillhole (its cross section is normally more than 200 times smaller than the total cross section) which each crossflow tray has for reasons of utility.

In other words, even at low loadings of the separating column, hydraulically sealed crossflow trays have accumulated liquid (reflux and feed liquid) and are at no risk of running dry. This results from the fact that the passages of hydraulically sealed crossflow trays are not chimneyless drillholes, as is the case in sieve trays. Rather, each passage opens into a chimney which prevents the tray from running dry. Above the chimney, vapor deflecting hoods (bubble-caps) are mounted and are immersed in the accumulated tray liquid. Frequently, the vapor deflecting hoods are slotted or serrated at their edges (i.e. they have transport slots). The vapor stream rising through the passage is deflected by the vapor deflecting hoods and flows parallel to the tray, i.e. at right angles to the column, into the accumulated liquid.

The vapor bubbles leaving adjacent hoods which are generally distributed equidistantly over the tray form a froth layer in the accumulated liquid.

Drainpipes or drain segments which leave the trays, generally to the left or to the right in alternation, supported by weirs, control the liquid level of the mass transfer trays and feed the liquid to the tray below. It is essential for the hydraulic sealing action that the drainpipes or drain segments of the upper tray are immersed in the accumulated liquid of the tray below. There are preferably no feed weirs. Bubble-caps which can be adjusted in height allow adaptation to the flow conditions and equalization of the immersion depths in the event of production irregularities, so that all bubble-caps of the tray have uniform gas flow.

Depending on the design and arrangement of the bubble-caps, the hydraulically sealed crossflow trays having single-flow configuration are divided, for example, into round bubble-cap trays (passage, chimney and bubble-cap are round), tunnel-cap trays (passage, chimney and bubble-cap are rectangular, the bubble-caps are arranged in succession, with the longer rectangular edge lying parallel to the crossflow direction of the liquid) and Thormann trays (passage, chimney and bubble-cap are rectangular, the bubble-caps are arranged in succession, with the longer rectangular edge at right angles to the crossflow direction of the liquid).

In this document, valve trays refer to crossflow trays which have tray drillholes having limited-stroke plate, ballast or lifting valves (floating flaps) which adapt the size of the vapor passage orifice to the particular column loading. The ascending gas stream is deflected, flows parallel to the tray into the accumulated reflux liquid and forms a froth layer. Drainpipes equipped with weirs conduct the reflux from tray to tray. Frequently, they have double-flow configuration. However, they may also have triple-flow and multiflow (for example up to octuple-flow) configuration.

It will be appreciated that the process according to the invention can also be employed when the rectification column is a tray rectification column of whose number of mass transfer trays at least 80% are hydraulically sealed crossflow mass transfer trays. The entire number of the mass transfer trays may also be hydraulically sealed crossflow trays. However, tray rectification columns are frequently used for the process according to the invention whose trays in the upper section of the rectification column are valve trays.

Preference is given in accordance with the invention to the hydraulically sealed crossflow trays being Thormann trays. This is the case especially when valve trays are used in the upper section of the rectification column.

The heat required for the process according to the invention is appropriately supplied, for example, via internal and/or external heat exchangers of conventional design and/or by means of jacket heating. Frequently, external circulation evaporators having natural or forced circulation are used.

It is possible in accordance with the invention to use a plurality of evaporators connected in series or parallel.

Thermal energy is preferably supplied in the process according to the invention by means of an external forced-circulation evaporator and more preferably by means of an external forced-circulation flash evaporator, as described, for example, in DE-A 10332758 and in EP-A 854129.

In contrast to the forced-circulation evaporator, the forced-circulation flash evaporator is separated from the rectification column by a throttle unit. A portion of liquid contents of the separating column at a pressure $P_x$ is continuously withdrawn and pumped by means of a circulation pump into the feed streams of, for example, a tubular evaporator (tube bundle heat exchanger). A heat carrier, for example heating steam (generally steam under pressure) which flows around the internal tubes of the tubular evaporator has a temperature above the temperature of liquid contents of the separating column. On the path through the feed and exit tubes of the tubular evaporator, the separating column liquid withdrawn is heated by indirect heat exchange to a temperature $T_{y'}$ which is above the temperature of liquid contents of the separating column.

A throttle unit separates tubular evaporator and separating column on the pressure side and enables, by suitable selection of the circulation pump output, the setting of a throttle inlet pressure $P_{y'}$ which is above $P_x$ and above the boiling pressure $P_{y'}$ of the separating column liquid withdrawn corresponding to the temperature $T_{y'}$. The aforementioned measures suppress boiling of the separating column liquid fraction circulated by pumping in the tubes of the tubular evaporator. The fraction of the separating column liquid which is circulated by pumping is actually superheated in the tubes of the tubular reactor with respect to the pressure $P_x$ above the liquid contents of the separating column, and the boiling process is thus shifted to the passage side of the throttle unit (i.e. the contents of the tubes of the tubular evaporator are monophasic and the tubular evaporator functions merely as a superheater). The superheated liquid can pass through the throttle unit into the separating column directly into the liquid contents of the separating column (of the separating column bottom). Under these conditions, the temperature of liquid contents of the separating column bottom regularly corresponds to the boiling temperature $T_x$ corresponding to the pressure $P_x$ above the bottoms liquid.

However, the superheated liquid may in principle also pass through the throttle unit into the separating column above the liquid level of the separating column bottom. Under these conditions, the temperature of the liquid contents of the separating column bottom is regularly below the boiling temperature $T_x$ corresponding to the pressure $P_x$ above the bottoms liquid. It is essential that the evaporative cooling action of the tubular evaporator, for example, mounted outside the separating column does not occur until inside the separating column, i.e. outside the circulation evaporator. The throttle may be, for example, mechanical (diaphragms, valves) and/or hydrostatic (by an appropriately high liquid column through the passage of the superheated liquid).

In the process according to the invention, the liquid F may be fed into the rectification column either into the bottom of the rectification column or into its lower section or into its middle section. The middle is defined via the number of theoretical plates of the rectification column. The midpoint of the theoretical plates (viewed from bottom to top) is the middle. The middle section is directly below and the lower section begins where the middle section ends, i.e. below the point in the rectification column where the first third of the theoretical plates ends (viewed from bottom to top).

Preference is given to carrying out the process according to the invention under reduced pressure. Top pressures which are particularly suitable in accordance with the invention are ≦500 mbar, and more preferably from 10 to 500 mbar, frequently from 10 to 200 mbar and preferably from 10 to 150 mbar. The pressure drop over the rectification column in the process according to the invention is advantageously from 300 to 100 mbar, or from 250 to 150 mbar. The temperature in the bottom of the rectification column in the process according to the invention is appropriately from 100 to 230° C. and preferably from 120 to 210° C., or from 160 to 200° C.

It will be appreciated that the separating internals present in the rectification column to be used in accordance with the invention may also be structured packings and/or random packings. Examples of useful random packings are rings, spirals, saddles, Raschig, Intos or Pall rings, barrel or Intalox saddles, Top-Pak or braids. All of the possible column internals mentioned in this document may of course also be present in the rectification column in mixed form.

As already mentioned, the other polymerization inhibitors in the process according to the invention are typically introduced at the top of the column. However, they may additionally also be added to the bottoms, and also already be present in the acrylic acid-containing liquid to be separated. Typical representatives of such polymerization inhibitors are once again phenothiazine, 4-methoxyphenol and 4-hydroxy-2,2,6,6-tetramethylpiperidine N-oxyl. Based on the acrylic acid content of the liquid phase, up to a few hundred ppm by weight of polymerization inhibitors are generally used.

It is also known (cf., for example, DE-A 10256147, DE-A 19501325 and Chem. Eng. Technol. 21 (1998) 10, p. 829 to 836) and equally applicable in accordance with the invention, for the purpose of additional polymerization inhibition, to pass a molecular oxygen-containing gas (for example air or lean air) through the rectification column during rectification (cf. also DE-A 10238145).

The withdrawal point E for the stream S in the process according to the invention may be disposed either at the top of the column or as a side withdrawal point below the top of the column (for example in the upper section or in the middle section of the rectification column). Preference is given in accordance with the invention to the latter.

Advantageously, the side withdrawal point is from at least 0.2 to 5 theoretical plates, frequently from 0.5 to 3 theoretical plates or from 0.6 to 2 theoretical plates, below the top of the column.

The acrylic acid-containing liquid to be separated in accordance with the invention may contain acrylic acid either in more or less pure form or in solution.

The solvent may be either aqueous or an organic solvent. The specific type of the solvent is substantially unimportant in accordance with the invention. It is preferably aqueous or an organic solvent possibly having small aqueous fractions.

The acrylic acid content in the liquid F may be ≧2% by weight, or ≧5% by weight, or ≧10% by weight, or ≧20% by weight, or ≧40% by weight, or ≧60% by weight, or ≧80% by weight, or ≧90% by weight, or ≧95% by weight, or ≧99% by weight.

In particular, the process according to the invention can be employed when the rectificative process relates to the removal of acrylic acid from a mixture comprising acrylic acid (generally from 10 to 35% by weight, frequently from 15 to 30% by weight, based on the weight of the liquid) and a (preferably inert) hydrophobic organic liquid having a higher boiling point than acrylic acid as main constituents and also (for example lower) aldehydes as secondary constituents (for example up to 10 000 or 5 000 ppm by weight) (a primary amine and/or its salt may have been added to the liquid F before its inventive rectificative treatment, as described, for example, in EP-A 717029), as occurs, for example, in the removal of acrylic acid from the reaction gas mixture of the catalytic gas phase oxidation in accordance with the procedures described in DE-A 44 36 243, DE-C 21 36 396, EP-A 925 272 and DE-A 43 08 087 or DE-A 10336386 (the stream S withdrawn usually contains not more than 99.5% by weight, frequently not more than 99% by weight and in many cases not more than 98.5% by weight, of acrylic acid). This is the case when the starting mixture for the process according to the invention, comprising acrylic acid and an inert hydrophobic organic liquid which has a higher boiling point than acrylic acid as main constituents and also lower aldehydes as secondary constituents, has been obtained, for example, from the reaction gas mixtures of the catalytic gas phase oxidation as the liquid effluent of a countercurrent absorption with subsequent desorption by stripping according to DE-C 21 36 39, EP-A 925 272 or DE-A 43 08 087 or DE-A 10336386, or as the liquid effluent of a countercurrent absorption with superimposed rectification according to DE-A 44 36 243. High-boiling inert hydrophobic organic liquid refers here to those liquids whose boiling point at atmospheric pressure (1 atm) is above the boiling temperature of acrylic acid and in which the solubility (% by weight, based on the weight of the solution) of acrylic acid oligomers and/or polymers is lower than in pure acrylic acid at 25° C. and 1 atm.

These are in particular high-boiling organic liquids which consist of at least 70% by weight of molecules which contain no externally active polar groups and are thus, for example, not capable of forming hydrogen bonds. In the narrower sense, the term includes here the high-boiling organic absorption liquids which are recommended in DE-C 21 36 396, DE-A 43 08 087 and also DE-A 44 36 243.

These are substantially liquids whose boiling point at atmospheric pressure is above 160° C. Examples include middle oil fractions from paraffin distillation, diphenyl ether, diphenyl or mixtures of the aforementioned liquids, for example a mixture of from 70 to 75% by weight of diphenyl ether and from 25 to 30% by weight of diphenyl (known as Diphyl). A favorable high-boiling hydrophobic organic absorption liquid is also a mixture consisting of a mixture of from 70 to 75% by weight of diphenyl ether and from 25 to 30% by weight of diphenyl, and also, based on this mixture, from 0.1 to 42.5% by weight of o-dimethyl phthalate.

In other words, the process according to the invention is suitable, inter alia, for liquids F which comprise the following components (the proportions are based on the total amount):

| | |
|---|---|
| Diphyl | 50 to 75% by weight, |
| dimethyl phthalate | 10 to 25% by weight, |
| diacrylic acid | 0.2 to 3% by weight, |

-continued

| | |
|---|---|
| acrylic acid | 15 to 35% by weight, frequently 15 to 25% by weight, |
| water | 0.07 to 0.2% by weight, |
| acetic acid | 0.01 to 0.2% by weight, |
| formic acid | 0.001 to 0.02% by weight, |
| propionic acid | 0.001 to 0.02% by weight, |
| phenothiazine | 0.01 to 0.1% by weight, |
| phthalic anhydride | 0.1 to 1% by weight, |
| benzoic acid | 0.2 to 2% by weight, |
| maleic anhydride | 0.1 to 2% by weight, |
| benzaldehyde | 0.1 to 1% by weight and |
| furfurals | 0.01 to 0.05% by weight. |

The rectification unit to be used may be of a design known per se and have the customary internals. Useful column internals are in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, spirals, saddles, Raschig, Intos or Pall rings, barrel or Intalox saddles, Top-Pak, etc., or braids. Particular preference is given to dual-flow trays.

In general, from 10 to 25 theoretical plates in the rectification unit are sufficient. The rectification is typically carried out under reduced pressure, preferably at a top pressure of from 70 to 140 mbar. The bottom pressure results from the top pressure, the number and the type of column internals, and also the fluid-dynamic requirements of the rectification and is preferably from 300 to 400 mbar.

When dual-flow trays are used as the separating internals, the hole diameter in the trays above the feed is generally from 5 to 25 mm, preferably from 10 to 20 mm. The hole diameter in the trays below the feed is typically from 15 to 80 mm, preferably from 25 to 50 mm, and is most preferably graduated, as described in the German patent application DE-A 10156988. The tray separation (the trays are generally arranged equidistantly) is typically from 300 to 700 mm, preferably from 350 to 400 mm, and most preferably 380 mm.

Preference is given to trace-heating the upper section of the rectification unit. In the case of a rectification unit having n theoretical plates, this relates to the region above the n/2th theoretical plate. The temperature of the trace heating is selected in such a way that no acrylic acid can condense on the internal column wall. This temperature is preferably from 5 to 10° C. above the boiling temperature of acrylic acid at the pressure present in the region in question in the rectification unit.

The rectification unit is typically manufactured from austenitic steel, preferably from the material 1.4571 (to DIN EN 10020).

The feed into the rectification unit is appropriately in its lower region. It is preferably from 2 to 5 theoretical plates-above the bottom of the rectification column. The feed temperature is typically 150° C.

The heat is supplied via internal and/or external heat exchangers (the heat carrier is again preferably steam) of conventional design and/or via jacket heating. It is preferably supplied via external circulation evaporators having natural or forced circulation. Particular preference is given to external circulation evaporators having forced circulation. It is possible to use a plurality of evaporators, connected in series or parallel. Preference is given to operating from 2 to 4 evaporators in parallel. The bottom temperature of the rectification unit is typically from 170 to 210° C., preferably from 180 to 200° C. The high boiler fraction which condenses in the bottom of the rectification column generally contains substantially the following constituents (the proportions are based on the total amount):

| | |
|---|---|
| Diphyl | 70-85% by weight, |
| dimethyl phthalate | 10-25% by weight, |
| diacrylic acid | 0.5-5% by weight, |
| acrylic acid | 0.2-2% by weight, |
| phenothiazine | 0.01-0.1% by weight, |
| phthalic anhydride | 0.1-1% by weight, |
| benzoic acid | 0.2-2% by weight, |
| maleic anhydride | 0.1-2% by weight, |
| benzaldehyde | 0.1-0.5% by weight and |
| furfurals | 0.01-0.05% by weight. |

The bottoms liquid which is withdrawn from the rectification unit and contains condensed high-boiling absorbent is partly discharged, preferably from 75 to 90% by weight based on the feed into the rectification unit, and partly recycled via a heat exchanger into the bottom region of the rectification column.

Crude acrylic acid is withdrawn via a sidestream above the feed into the rectification column, preferably from 8 to 20 theoretical plates above the column bottom. Withdrawal of the crude acrylic acid is effected in a customary manner and is subject to no restriction. It is suitable to withdraw it via a collecting tray, in which case the entire reflux is collected and a portion is discharged and the other portion is used as reflux below the collecting tray, or using a tray having an integrated removal means, preferably using a dual-flow tray having an integrated removal means. The crude acrylic acid withdrawn normally contains substantially the following constituents (the proportions are based on the total amount):

| | |
|---|---|
| acrylic acid | 98-99.9% by weight, |
| acetic acid | 0.05-0.3% by weight, |
| water | 0.001-0.05% by weight, |
| formic acid | 0.001-0.005% by weight, |
| propionic acid | 0.01-0.05% by weight, |
| furfurals | 0.01-0.05% by weight, |
| allyl acrylate | 0.001-0.01% by weight, |
| benzaldehyde | 0.001-0.01% by weight, |
| maleic anhydride | 0.002-0.02% by weight, |
| diacrylic acid | 0.01-0.05% by weight and |
| phenothiazine | 0.01-0.05% by weight. |

The crude acrylic acid withdrawn is cooled by means of cold crude acrylic acid (obtained beforehand) and/or by means of a heat exchanger (an example of a suitable coolant is surface water). It is possible to use a plurality of heat exchangers, connected in series or parallel. In the heat exchangers, which are known per se to those skilled in the art and are subject to no particular restriction, the crude acrylic acid is preferably cooled by from 40 to 70° C.

The crude acrylic acid withdrawn, preferably from 10 to 25% by weight based on the feed into the rectification column, is discharged and partly used as the solvent for the polymerization inhibitor.

The low boiler stream removed at the top of the rectification column can be cooled indirectly, for example by heat exchangers (the coolant used may, for example, be surface water), which are known per se to those skilled in the art and are subject to no particular restriction, or directly, for example by a quench. It is preferably cooled by direct cooling. To this end, low boiler fraction which has already been condensed is cooled by means of a suitable heat exchanger and the cooled liquid is sprayed in the vapor above the withdrawal point. This spraying can be effected in a separate apparatus or in the rectification unit itself. In the case of spraying in the rectification unit, the withdrawal point of the low boiler fraction is advantageously configured as a collecting tray. Internals which improve the mixing of the cooled low boiler fraction with the vapor can be used to increase the effectiveness of the direct cooling. Useful for this purpose are in principle all common internals, for example trays, structured packings and/or random packings. Among the trays, preference is given to bubble-cap trays, sieve trays, valve trays, Thormann trays and/or dual-flow trays. Among the random packings, preference is given to those comprising rings, spirals, saddles, Raschig, Intos or Pall rings, barrel or Intalox saddles, Top-Pak, etc., or braids. Particular preference is given to dual-flow trays. In general, from 2 to 5 theoretical plates are sufficient here. These trays are not taken into account in the information given hitherto on the number of theoretical plates of the rectification unit. The direct condensation of the low boiler fraction may also be carried out in a plurality of stages, with a temperature decreasing upward. The low boiler stream removed via the top of the rectification column contains substantially the following components (the proportions are based on the total amount):

| | |
|---|---|
| acrylic acid | 90-99% by weight, |
| acetic acid | 0.5-3% by weight, |
| water | 0.5-2% by weight, |
| phenothiazine | 0.02-0.1% by weight, |
| allyl acrylate | 0.01-0.1% by weight, |
| furfurals | 0.002-0.01% by weight, |
| propionic acid | 0.01-0.05% by weight, |
| formic acid | 0.1-1% by weight and |
| acrolein | 0.001-0.002% by weight. |

A portion of the liquid withdrawn as the low boiler fraction, preferably from 36 to 50% by weight based on the feed into the rectification column, is used as reflux; the remainder of the low boiler fraction, preferably from 0.5 to 2% by weight based on the feed into the rectification column, is discharged. In a manner which is advantageous in accordance with the invention, the rectification described is then operated in such a way that the diacrylic acid content in the reflux, based on its weight, is at least 550 ppm by weight. The aforementioned diacrylic acid content is preferably 1 000 ppm by weight or even 1 500 ppm by weight or more.

The offgas from the rectification unit generally contains substantially the following constituents (when the oxygen or air coinhibition still to be detailed hereinbelow is employed; the proportions are based on the total amount):

| | |
|---|---|
| nitrogen | 70-80% by weight, |
| oxygen | 15-25% by weight, frequently from 15 to 21% by weight, |
| acrylic acid | 1-5% by weight, |
| acetic acid | 0.05-0.5% by weight, |
| water | 0.2-0.8% by weight, |
| acrolein | 0.001-0.005% by weight, |
| formic acid | 0.02-0.2% by weight, |
| allyl acrylate | 0.001-0.005% by weight and |
| carbon oxides | 0.02-0.06% by weight. |

The offgas is incinerated together with the other production residues.

The polymerization inhibitors used in the rectification column may be alkylphenols, for example o-, m- or p-cresol (methylphenol), 2-tert-butyl-4-methylphenol, 6-tert-butyl-2, 4-dimethylphenol, 2,6-di-tert-butyl-4-methylphenol, 2-tert-butylphenol, 4-tert-butylphenol, 2,4-di-tert-butylphenol, 2-methyl-4-tert-butylphenol, 4-tert-butyl-2,6-dimethylphenol, or 2,2'-methylenebis(6-tert-butyl-4-methylphenol), hydroxyphenols, for example hydroquinone, 2-methylhydroquinone, 2,5-di-tert-butylhydroquinone, pyrocatechol (1,2-dihydroxybenzene) or benzoquinone, aminophenols, for example para-aminophenol, nitrosophenols, for example para-nitrosophenol, alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol, tocopherols, for example α-tocopherol, or else 2,3-dihydro-2,2-dimethyl-7-hydroxybenzofuran (2,2-dimethyl-7-hydroxycoumaran), N-oxyls such as 4-hydroxy-2,2,6,6-tetramethylpiperidine N-oxyl, 4-oxo-2,2,6,6-tetramethyl-piperidine N-oxyl, 4-acetoxy-2,2,6,6-tetramethylpiperidine N-oxyl, 2,2,6,6-tetramethyl-piperidine N-oxyl, 4,4',4''-tris(2,2,6,6-tetramethylpiperidine N-oxyl) phosphite or 3-oxo-2,2,5,5-tetramethylpyrrolidine N-oxyl, aromatic amines or phenylenediamines, for example N,N-diphenylamine, N-nitrosodiphenylamine, N,N'-dialkyl-para-phenylene-diamine, where the alkyl radicals may be the same or different and each independently consist of from 1 to 4 carbon atoms and may be straight-chain or branched, hydroxylamines, for example N,N-diethylhydroxylamine, phosphorus compounds, for example triphenylphosphine, triphenyl phosphite, hypophosphorous acid or triethyl phosphite, sulfur compounds, for example diphenyl sulfide or phenothiazine, optionally in combination with metal salts, for example the chlorides, dithiocarbamates, sulfates, salicylates or acetates of copper, manganese, cerium, nickel or chromium. It will be appreciated that mixtures of the polymerization inhibitors mentioned may also be used.

Preference is given to using phenothiazine as the polymerization inhibitor in the rectification unit, or another polymerization inhibitor which exhibits the same effectiveness as phenothiazine.

The polymerization inhibitor is preferably added to the condensed low boiler reflux as a solution in relatively pure acrylic acid, more preferably as a solution in the crude acrylic acid removed via the sidestream. The total concentration of aldehydic impurities in the acrylic acid used for the stabilizer mixture is preferably less than 500 ppm by weight. The stabilizer (inhibitor) concentration in the stabilizer mixture (in the stabilizer solution) depends on the stabilizer used and the solvent used. The optimum stabilizer concentration in the stabilizer mixture may be determined by dissolution experiments and, in the case of phenothiazine as the stabilizer and of crude acrylic acid as the solvent, is from 0.1 to 2% by weight, preferably from 1.2 to 1.7% by weight. The stabilizer is metered in such a way that the stabilizer concentration in the discharged crude acrylic acid is from 50 to 500 ppm by weight, preferably from 150 to 350 ppm by weight.

The form of the solid polymerization inhibitors which are introduced into the stabilizer mixture vessel is in principle arbitrary. Useful forms are, for example, flakes, granules or pellets. Owing to the low dust fraction and the more favorable flow behavior, preference is given to pellets. The solid polymerization inhibitors may be introduced into the stabilizer mixture vessel, for example by means of conveying screws, from a silo.

To further support the stabilization (polymerization inhibition), an oxygenous gas, preferably air or a mixture of air and nitrogen (lean air), more preferably air, may be present.

This oxygenous gas is preferably metered into the bottom region of the rectification column and/or into a circulation evaporator.

The air is appropriately withdrawn directly from the atmosphere, preferably at one or more sampling points.

Preference is given in accordance with the invention to likewise filtering the air used in this way before its use, as already described in connection with the partial oxidation.

Very particular preference is given to using air having a salt content, for example of organic and inorganic chlorides, in particular of alkali metal chlorides, of less than 10 ppm by weight.

The oxygenous gas is metered in such a way that the partial oxygen pressure at the top of the rectification unit is at least 0.5 mbar, preferably at least 2 mbar.

In addition, a surfactant can be metered into the rectification unit, as described, for example, in DE-A 19810962.

However, the process according to the invention can also be applied to the rectificative further purification of acrylic acid qualities which already contain from 95 to 99.5 or 99.8% by weight of acrylic acid (it is especially favorable when they contain $\geq 2$, or $\geq 5$ ppm by weight, or $\geq 10$ ppm by weight, or $\geq 20$ ppm by weight, or $\geq 50$ ppm by weight, of aldehydes, for example acrolein, furfurals, benzaldehyde, etc; especially when their boiling point at atmospheric pressure (1 atm) is below the boiling point of acrylic acid). These may have been treated before the rectification with amines such as hydrazine or hydrazine derivatives (for example aminoguanidine hydrogencarbonate), as described, for example, in DE-A 10219592, EP-A 713854 and EP-A 270999.

EXAMPLES AND COMPARATIVE EXAMPLE

Four samples, each of 0.5 ml, whose content of acrylic acid was in all cases 99.8% by weight were freshly prepared (distillation, then freezing).

Subsequently, the diacrylic acid content of the four samples was set to the following values by adding substantially pure diacrylic acid:

Sample 1: $\leq 5$ ppm by weight;
Sample 2: 500 ppm by weight;
Sample 3: 1000 ppm by weight;
Sample 4: 1500 ppm by weight;
Sample 5: 10000 ppm by weight;
Sample 6: 15000 ppm by weight.

There was no further polymerization inhibitor in the acrylic acid samples. In addition, sufficient benzaldehyde was added to all four samples that they had a benzaldehyde content of 500 ppm by weight.

Under an air atmosphere, each of the samples was transferred to a 1.8 ml glass ampule. Immediately after completion, the ampules were stored at 120° C. under rotation in a forced-air drying cabinet, in order to ensure complete mixing. The time T until complete polymerization of the particular sample was then determined visually.

The experimental series was repeated three times and the value calculated was arithmetically averaged.

The average results for the time T of the particular samples were:

Sample 1: 128 min;
Sample 2: 136 min;
Sample 3: 143 min;
Sample 4: 153 min;
Sample 5: 175 min;
Sample 6: 195 min.

U.S. Provisional Application No. 60/509,540, filed on Oct. 9, 2003, is incorporated into the present application by reference.

With regard to the abovementioned teachings, numerous alterations and deviations from the present invention are possible. It may therefore be assumed that the invention, within the scope of the amended claims, may be performed differently than specifically described herein.

We claim:

1. A process for rectificatively separating an acrylic acid-containing liquid F by feeding the acrylic acid-containing liquid F to a rectification column via a feed point Z and withdrawing a stream S at a withdrawal point E above the feed point Z of the rectification column, said stream S having a content of acrylic acid, based on the weight of the stream S, which is $\geq 90\%$ by weight and is greater than the corresponding acrylic acid content of the liquid F in % by weight, wherein the diacrylic acid content G of the reflux liquid within the region of the rectification column at least two theoretical plates above the feed point Z is at least in places $\geq 550$ ppm by weight based on the weight of the reflux liquid.

2. The process as claimed in claim 1, wherein the diacrylic acid content G of the reflux liquid is $\geq 650$ ppm by weight.

3. The process as claimed in claim 1, wherein the diacrylic acid content G of the reflux liquid is $\geq 1000$ ppm by weight.

4. The process as claimed in any of claims 1 to 3, wherein the diacrylic acid content G of the reflux liquid is satisfied within the entire region of the rectification column at least two theoretical plates above the feed point Z.

5. The process as claimed in any of claims 1 to 3, wherein the diacrylic acid content G of the reflux liquid is satisfied within the entire region of the rectification column at least four theoretical plates above the feed point Z.

6. The process as claimed in claim 4, wherein the withdrawal point E is at least two theoretical plates above the feed point Z of the rectification column.

7. The process as claimed in claim 4, wherein the liquid F to be separated comprises an added Brønsted acid having a lower boiling point than acrylic acid and $pK_a \leq 16$.

8. The process as claimed in claim 4, wherein diacrylic acid as such and/or diacrylic acid-containing acrylic acid are added to the reflux liquid.

9. The process as claimed in claim 4, wherein the rectification column comprises at least one sieve tray as a separating internal.

10. The process as claimed in claim 4, wherein the rectification column comprises at least one hydraulically sealed crossflow tray as a separating internal.

11. The process as claimed in claim 4, wherein the thermal energy required for the process according to the invention is supplied via an external forced-circulation flash evaporator.

12. The process as claimed in claim 11, wherein the forced-circulation flash evaporator is a tubular evaporator.

13. The process as claimed in claim 4, wherein the liquid F is a mixture which comprises from 10 to 35% by weight of acrylic acid, from 50 to 80% by weight of a hydrophobic organic liquid having a higher boiling point than acrylic acid and up to 5000 ppm by weight of aldehyde.

14. The process as claimed in claim 4, wherein the liquid F comprises the following components:

| | |
|---|---|
| Diphyl | 50 to 75% by weight, |
| dimethyl phthalate | 10 to 25% by weight, |
| diacrylic acid | 0.2 to 3% by weight, |

-continued

| | |
|---|---|
| acrylic acid | 15 to 35% by weight, frequently 15 to 25% by weight, |
| water | 0.07 to 0.2% by weight, |
| acetic acid | 0.01 to 0.2% by weight, |
| formic acid | 0.001 to 0.02% by weight, |
| propionic acid | 0.001 to 0.02% by weight, |
| phenothiazine | 0.01 to 0.1% by weight, |
| phthalic anhydride | 0.1 to 1% by weight, |
| benzoic acid | 0.2 to 2% by weight, |

-continued

| | |
|---|---|
| maleic anhydride | 0.1 to 2% by weight, |
| benzaldehyde | 0.1 to 1% by weight and |
| furfurals | 0.01 to 0.05% by weight. |

15. The process as claimed in claim 4, wherein the liquid F contains from 95 to 99.8% by weight of acrylic acid.

* * * * *